United States Patent [19]

Leeb et al.

[11] Patent Number: 5,176,026
[45] Date of Patent: Jan. 5, 1993

[54] APPARATUS FOR MEASURING THE SURFACE HARDNESS OF BUILDING MATERIALS

[75] Inventors: Dietmar Leeb, Kilchberg; Ueli Brunner, Dubendorf, both of Switzerland

[73] Assignee: Proceq S.A., Zurich, Switzerland

[21] Appl. No.: 622,844

[22] Filed: Dec. 5, 1990

[30] Foreign Application Priority Data

Dec. 7, 1989 [CH] Switzerland .................. 4397/89

[51] Int. Cl.⁵ .................................................. G01N 3/30
[52] U.S. Cl. .................................................. 73/79
[58] Field of Search ..................... 73/79, 81, 82, 12

[56] References Cited

U.S. PATENT DOCUMENTS

| | | | |
|---|---|---|---|
| 3,576,127 | 4/1971 | Weitzel et al. | 73/79 |
| 3,669,261 | 6/1972 | Moulin | 73/79 |
| 3,879,982 | 4/1975 | Schmidt | 73/79 |
| 4,631,951 | 12/1986 | Bohm | 73/3 |
| 4,674,317 | 6/1987 | Cohrs et al. | 73/3 |
| 4,885,933 | 12/1989 | Hiestand et al. | 73/79 |
| 5,047,629 | 9/1991 | Geist | 250/231.1 |

FOREIGN PATENT DOCUMENTS

| | | | |
|---|---|---|---|
| 0001950 | 1/1988 | Japan | 73/79 |
| 978010 | 6/1981 | U.S.S.R. | |

Primary Examiner—Robert Raevis
Attorney, Agent, or Firm—Ladas & Parry

[57] ABSTRACT

An apparatus for measuring the surface hardness of building materials, having a housing comprising a test hammer, a driving spring and an impact pin, said test hammer being moveable by means of said driving spring along a path in said housing to be brought to impact against said impact pin, which for measurement is placed on the surface to be measured, and further having measuring device for measuring a rebound height of said test hammer wherein said test hammer is provided with an optical pattern extending over at least part of its length and wherein said measuring device comprises an optical detection unit arranged adjacently to said path of the test hammer and provided for detecting said optical pattern of the test hammer, and wherein said measuring device further comprises an evaluation circuit connected to said optical detection unit to determine the maximum height of the rebounding hammer at the upper end of its path after impact.

10 Claims, 4 Drawing Sheets

APPARATUS FOR MEASURING THE SURFACE HARDNESS OF BUILDING MATERIALS

BACKGROUND OF THE INVENTION

1. Field of the Invention

The invention refers to an apparatus for measuring the surface hardness of building materials, as e.g. of concrete. The apparatus is provided with a test hammer which by spring force is driven and brought to impact against an impact pin resting on the surface to be measured. Furthermore, a measuring device is provided for determining the rebound height of the test hammer after said impact. The measured rebound height then is a measure for the hardness of the respective building material which is not destroyed by this measuring process.

2. Description of the Prior Art

An apparatus of this type is known as Schmidthammer and is widely used today. Its basic principle is disclosed in Swiss Patent specification No. 283 099. As already mentioned, the known apparatus comprises a test hammer, which is driven by spring force to impact against an impact pin, which is placed on the surface of a concrete element to be measured. By the force of the impact, the pin which has a spherically shaped tip slightly penetrates the concrete surface, whereby part of the impact energy is dissipated. The remaining energy then causes the hammer to jump back or rebound against the force of the spring. The rebound height of the hammer as a percentage of its forward path (i.e. the path from the beginning of the spring force action to the impact on the impact pin) is designated as a rebound value R. This value R is characteristic for the elastic and plastic behavior of the concrete near its surface.

From this R-value the compression strength of the concrete can be derived under certain conditions. This is done by means of empirical calibrations curves, in which each R-value is related to a corresponding compression strength value.

In the known apparatus called Schmidthammer the rebound height is measured on purely mechanical basis by means of a drag pointer which is taken along by the rebounding hammer.

The upper end position of the drag pointer then indicates the rebound height, which can be read on a scale arranged at the housing of the apparatus. The drag pointer is guided on a linear guide and must have a defined friction when displaced along this guide. The friction value has to be in the range between 50 g and 80 g to prevent any displacement of the drag pointer above the real rebound height on the one hand and to avoid excessive braking of the test hammer by the drag pointer on the other hand. Especially because of the fact that the pointer guide gets dirty during use, the friction of the drag pointer has often to be measured and readjusted. A further drawback of the known apparatus results from the relatively coarse scale which for reasons of readability can not be made very fine. The reading and recording of the measured values has to be done immediately after the test stroke while the apparatus remains placed on the concrete surface in order to avoid any displacement of the draw pointer by shaking the apparatus. This is at least unpractical and in certain positions of the apparatus even difficult. An automatic processing of the measured values is not possible.

SUMMARY OF THE INVENTION

Therefore, it is an object of the invention to provide a new apparatus of the above mentioned type, by which said rebound value R which is characteristic for the surface hardness can automatically be determined by a contact-less measurement of the rebound height of the hammer to avoid the above discussed drawbacks.

It is a further object of the invention to provide a new apparatus of the above mentioned type, the function of which is not affected by changing friction of mechanical parts.

Still a further object of the invention is to provide a new apparatus of the above type in which the rebound height can be determined more exactly and independently from reading of a measuring scale.

These and other objects which will become clear as the description proceeds are achieved by providing the test hammer over at least part of its length with an optical pattern, by arranging an optical detection unit adjacent to the path of the hammer in order to detect said optical pattern at the rebounding hammer and by evaluating the signals of the optical sensor in an evaluation circuit to determine the exact return position of the test hammer at the upper end of its rebounding path.

BRIEF DESCRIPTION OF THE DRAWINGS

The present invention will be better understood and objects other than those set forth above will become apparent when consideration is given to the following detailed description thereof. Such description makes reference to the annexed drawings, wherein.

DESCRIPTION OF THE PREFERRED EMBODIMENTS

Figures 1, 2, 3:
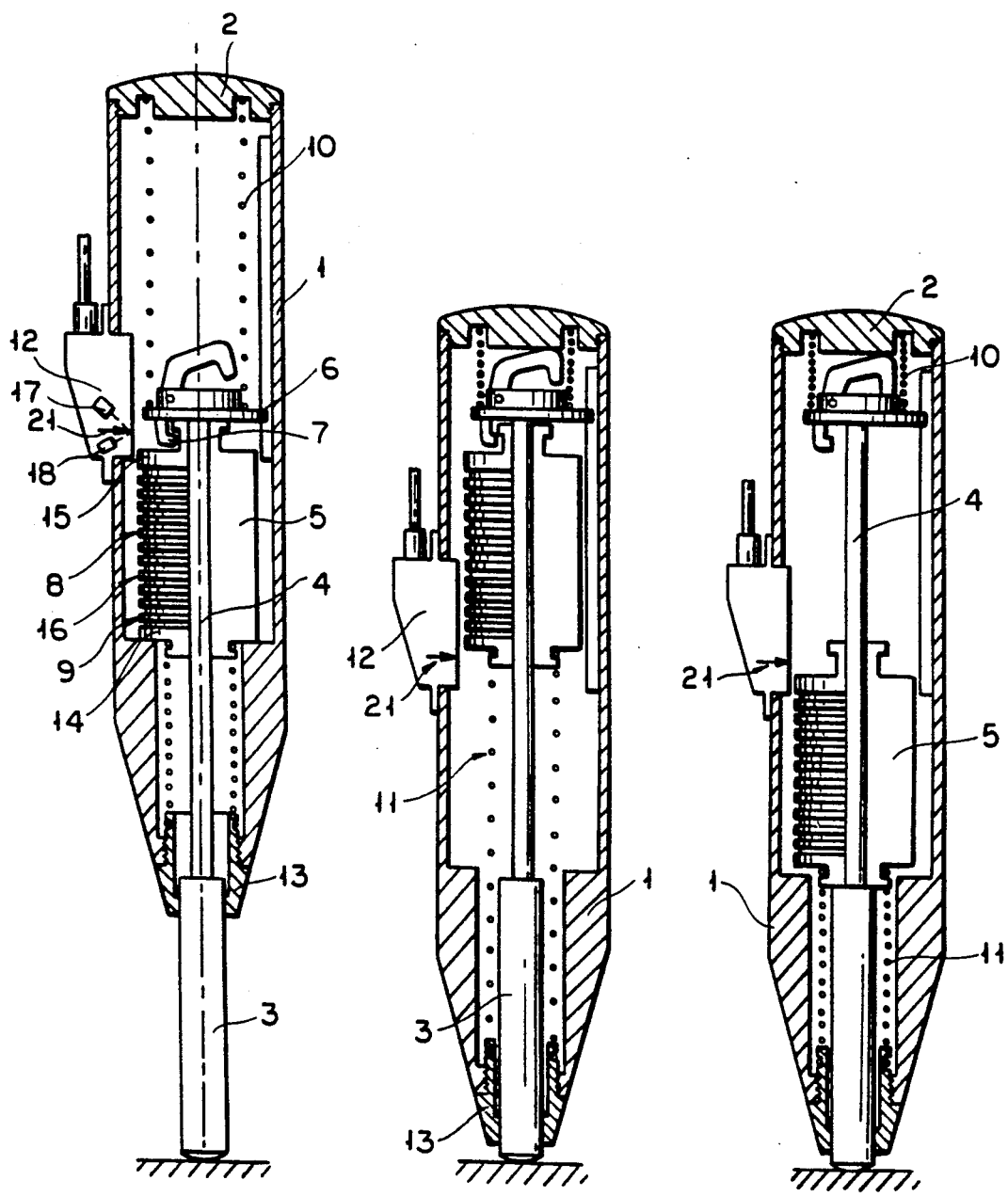
FIG. 1 is a side view, partly in cross section, of the apparatus of the invention, in its initial position.
FIG. 2 is a side view substantially as in FIG. 1 in a position with a tensioned driving spring for the hammer.
FIG. 3 is a side view substantially as in FIG. 1 and 2 with the hammer in its impact position.

Based on the FIGS. 1 to 3 the mechanical construction of the measuring apparatus of the invention is explained first. Each of these figures shows a certain defined operation phase of the same measuring apparatus. In FIG. 1 the measuring apparatus is in its initial state, whereas FIG. 2 shows a position of the apparatus immediately before the measuring procedure is started. Finally, FIG. 3 exhibits the apparatus in a state after the measuring procedure.

As can be seen from these figures the measuring apparatus of the invention comprises a housing 1 with a cylindric test hammer 5 to which a tension spring 11 is mounted for driving the test hammer 5 downwards against an impact pin 3. The impact pin 3 is displaceably guided within a guiding collar 13 arranged at the front end of the apparatus. At the rear end of the impact pin 3 a guiding bar 4 is mounted, on which the test hammer 5 is slidingly guided. The guiding bar 4 ends with a guiding disc 6 engaging a lateral guide rail mounted to said housing 1 to prevent any rotation of the impact pin 3. A jack 7 is mounted to the guiding disc 6 for engaging the rear end of the test hammer 5 and holding the same back when the driving spring 11 is tensioned. Said jack 7 is opened when coming into contact with a cover 2 of the housing 1 whereby the measuring stroke is initiated and the hammer 5 is released (see FIG. 2). Between the guiding disc 6 and the cover of the housing a loading spring 10 is provided which is a compression spring for urging said jack 7 together with the guiding bar 4 and the impact pin 3 into their outer position (see FIG. 1), in which said jack 7 engages the test hammer 5 again for a following tensioning of the driving spring 11 by pressing the housing 1 down (see FIG. 2). This construction substantially corresponds to the one of a known concrete testing apparatus and therefore needs not to be described in more detail here.

In contrast to the known devices, the test hammer 5 of the invention is provided with an optical pattern 8 at its cylindric outer surface, as can be seen from FIG. 1.

The optical pattern 8 substantially comprises successive circular strips 9, 16 of equal width arranged at the hammer surface, which strips alternatingly are light reflecting and light absorbing. In the embodiment shown in FIG. 1 these strips are formed by grooved recesses 9 having a light absorbing coating and non-recessed surface zones 16 having a reflection coating. However, it has to be noted that in FIG. 1 the arrangement of recesses 9 and reflecting zones 16 is shown only schematically. In fact, the width of the light absorbing recesses 9 and of the non-recessed reflecting zones 16 is substantially smaller, e.g. 0.4 mm each. There is a total of about 29 recesses 9 and of about 30 reflecting zones 16 in an embodiment of the invention. Preferably, the optical pattern is not made substantially finer so that the presence of dirt on the pattern does not affect the optical detection thereof. The measuring accuracy, however, is substantially better than the width of the strips 9, 16 as will be explained below.

On the housing 1 an optical detection unit 12 is mounted. This optical detection unit 12 comprises combined infrared-light emitter 17 and light sensor 18. At the place marked with an arrow 21 in the figures a slit diaphragm is arranged, the slit of which extends perpendicularly to the direction of displacement of the test hammer 5 and the position of which defines the zero point of the measurement. Through this slit diaphragm an infrared diode of the infrared-light emitter 17 illuminates the pattern 8 of the hammer 5 under a defined angle. An infrared light sensor 18 is arranged in a corresponding reflection angle thereto. The infrared light emitted through the slit diaphragm onto the surface of the test hammer 5 is reflected back from the reflecting zones 16 into the light sensor and converted therein into electrical signals corresponding to the received light intensity. In the following the position of the light sensor 18 will be designated by the numeral 21 and symbolized by an arrow in the figures.

Accordingly, when the hammer 5 passes in front of the optical detection unit 12, the sensor 21 receives reflected infrared light pulses interrupted by "dark" intervals. The number of detected light pulses then corresponds to the number of reflecting zones 16, which passed in front of the optical detection unit.

When the test hammer 5 rebounds after the impact onto the impact pin 3, the rebounding height therefore can be determined based on the signals from the optical detection unit as will be explained in detail below.

Thereby, the mentioned strips 9, 16 on the test hammer 5 preferably are not only counted but for each strip of the pattern a time value is determined corresponding to the time while a reflection pulse (or a dark interval) is detected through the slit diaphragm. For this purpose a timer 25 is provided in the evaluation circuit which is started, when the optical sensor 18 begins to receive a light pulse and which continues its count during this light pulse. When this light pulse ends, i.e. no light is received any-more, the timer is stopped, its actual count is recorded and it is started again immediately.

It then counts during the "dark" interval until light is received again. At this moment the timer 25 is stopped and started again and its actual count is recorded, as already explained.

Therefore, the timer 25 connected to the light sensor 21 is started at each transition from a reflecting zone 16 to an absorbing recess 9 and vice versa and is stopped at each next such transition. For triggering said timer 25, which is part of a microprocessor $\mu P$ (FIG. 6) a Schmidt-trigger circuit 22 is provided which is connected to the light sensor 21.

The signal generated by the pattern 8 of the rebounding test hammer 5 in the light sensor 18 therefore is a wave signal with a wavelength which is characteristic for the actual velocity of the hammer. The working point of the mentioned Schmidt-trigger circuits 22 corresponds to the zero passage of the wave signal and for each strip of the pattern 8 (i.e. each half wave in the sensor signal) there is a count of the timer 25 which corresponds to the mentioned wave length, i.e. to the above mentioned time value for each strip of the pattern 8. As a result of each measurement, a sequence of counts of the timer 25 is recorded in the microprocessor, which sequence is evaluated as will be explained below.

Figure 6:
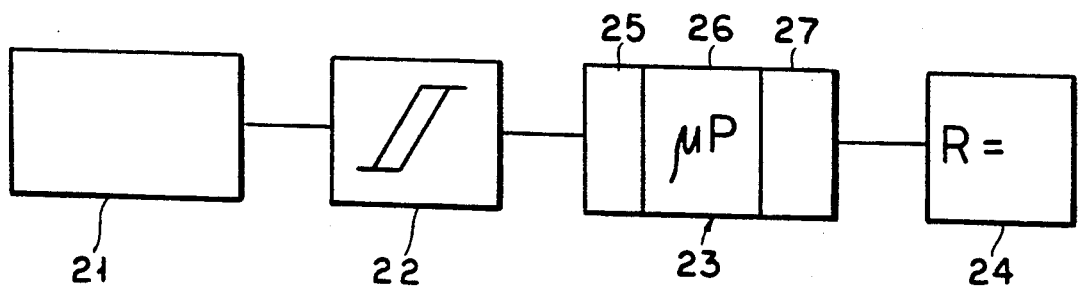
FIG. 6 is a block diagram of an evaluation circuit.

In FIG. 6 an evaluation circuit is shown having a light sensor 21 (i.e. an infrared light receiver, as explained above) which is connected to a Schmidt-trigger circuit 22 for deriving binary start- and stop-signals from the received sensor signal for starting and stopping a timer 25/microprocessor 23, in which the timer counts are recorded and evaluated to determine an R-value. Said microprocessor further comprises a processor unit 26 and a store 27 for said time counts. On a display unit 24 the determined R-value will be displayed.

The mentioned sequence of counts of the timer/microprocessor 23 allows a quick and exact evaluation of the measuring result as will be explained. First, the measuring procedure is described based on FIG. 4. In this figure only the test hammer 5 and the impact pin 3 are shown in three consecutive phases of the measurement. An arrow indicates the position of the light sensor 21. In the left part of this figure the initial position of the test hammer 5 is shown before a measuring stroke is released. The center of FIG. 4 exhibits the situation at the moment of impact of the test hammer 5 onto the impact pin 3 and its right part is the situation, when the hammer 5 has reached its uppermost rebounding position. Therein $h_A$ indicates the length of the forward movement of the test hammer 5 before impact and $h_R$ is the rebound height of the hammer 5. The R-value then is given by the equation:

$$R = 100 * (h_R/h_A) \qquad (1)$$

Figure 4:
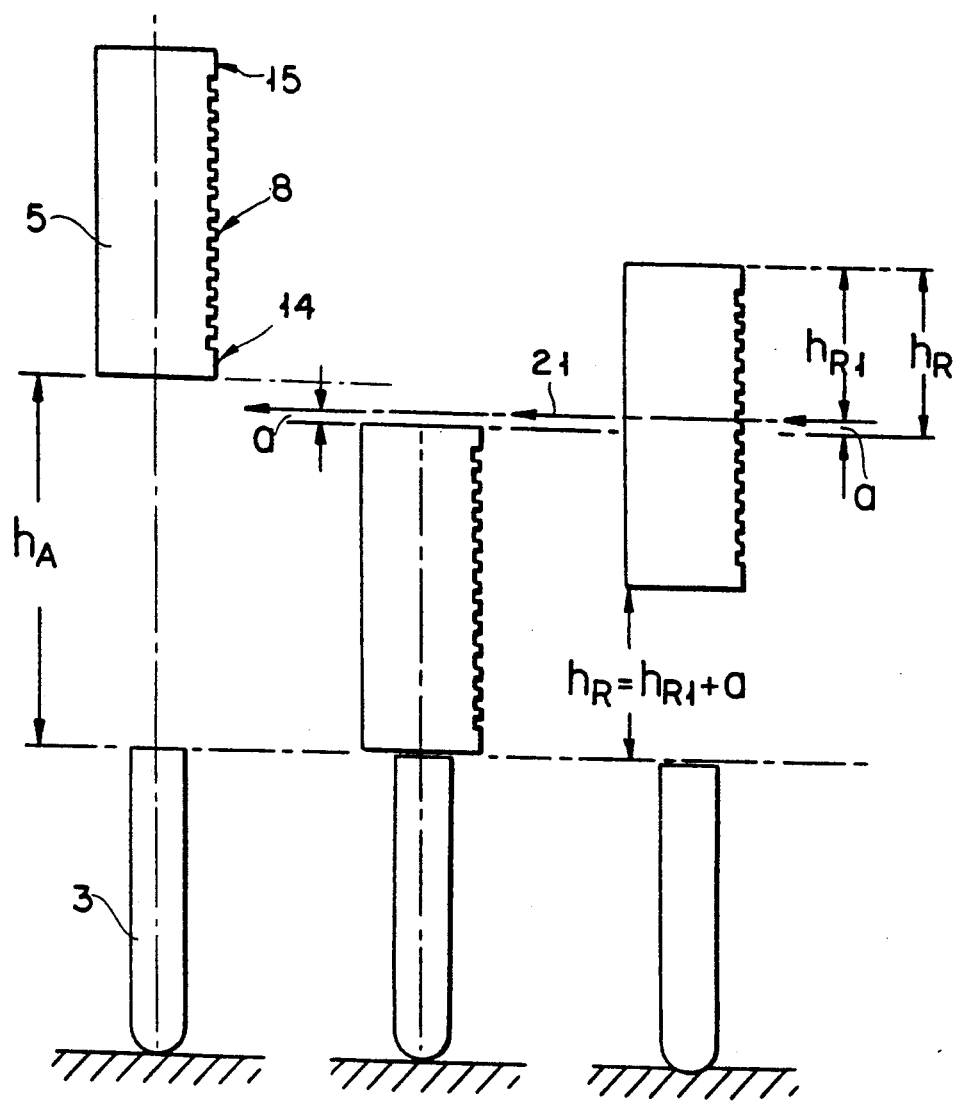
FIG. 4 is a diagram showing three characteristic positions of the hammer before during and after impact.

However, what in fact is measured by the light sensor 21 indicated by arrows in FIG. 4 is a reduced height value $h_{R1}$. In order to determine the effective rebound height $h_R$ an adjustment value a has to be added to the measured height value $h_{R1}$. Consequently:

$$h_R = h_{R1} + a \quad (2)$$

The adjustment value a depends on the position of the diaphragm 21 at the housing 1 of the measuring apparatus and can be adjusted by time measurement, as will be described.

As can be seen from FIG. 1 and FIG. 4 the optical pattern 8 on the test hammer 5 on its upper and its bottom end is limited by reflecting zones 14, 15 of greater width. These end zones 14, 15 of the optical pattern 8 preferably have an extension of about three times the extension of the other strips of the pattern. Thereby, a secure triggering of the timer 23 is achieved at the upper and the bottom end of the optical pattern 8, even if the pattern partly is dirty or damaged.

In the following a measuring and evaluation cycle is described based on FIG. 4 and the above description thereof.

When a measuring stroke is released (see FIG. 2 and FIG. 4, left part) the test hammer 5 moves downwards driven by the driving spring 11. The complete optical pattern 8 at its surface thereby passes the light sensor 18 and a first sequence of counts is generated comprising 30 individual counts for the reflecting zones, and 29 individual counts for the light absorbing recesses, each count corresponding to a time a reflecting zone 16 or recess 9 needed for passing the light sensor 18. The first and the last count of the sequence corresponding to the extended end zones 14, 15 of the pattern are substantially higher than the adjacent counts. Therefore, this first sequence of counts has a clearly defined structure. In a first phase of the measuring cycle the evaluation circuit 23 checks the described structure of this first sequence of counts. If this structure can not be found, it is an indication for a false function, e.g. due to dirt on the optical pattern 8, and the measurement is rejected already in this phase. If, on the other hand, the above structure can be verified, this is an indication of correct operation and the following measurement of the rebound height will be accepted. Therefore, this first phase of the measuring cycle serves to verify the proper function of the system.

Furthermore, the individual counts measured during the first measuring cycle give an indication for the impact velocity of the test hammer 5 and for its impact energy, which depends in the condition of the driving spring 11. The measurement is only correct if the impact energy of the test hammer 5 remains within a certain range. The counts measured in the first measuring cycle therefore allow to check this condition, also. If the impact energy falls below a defined threshold value the measurement is rejected and the driving spring 11 has to be exchanged.

After the described first measuring phase the test hammer 5 is in the position shown in the center of FIG. 4. In this position, i.e. immediately before and after the impact of the test hammer 5 the light sensor 21 does not receive any light signal for a longer time interval. This time interval between the last signal of the first measuring cycle and the first signal of the following second rebounding cycle is measured by the timer/microprocessor 23 as a return interval $T_u$. This return interval $T_u$ indicates the beginning of the rebounding cycle and simultaneously is a direct measure for the above mentioned adjustment value a, because the interval $T_u$ increases together with the value a as can be seen from FIG. 4 (center).

Therefore the adjustment value a of equation (2) for calculating the effective rebounding height is determined by measuring the time interval $T_u$. Accordingly, a mechanical adjustment of the light sensor 18 or the optical detection unit 12 at the housing 1 is not necessary, since the value of a can be determined and corrected for each measurement by measuring the time interval $T_u$.

After the time interval $T_u$ the optical pattern 8 of the rebounding test hammer 5 passes the optical sensor 18 again but in upward direction with decreasing speed. When the test hammer 5 reaches its maximum rebound height $h_R$, the direction of its movement is reversed and it moves downwards again with increasing speed. Obviously, the counts measured by the timer 25 and derived from the optical pattern 8, are biggest immediately before and after the test hammer 5 reaches its maximum rebound height. If the sequence of counts measured during the above described rebounding cycle are analyzed, it is clear that the maximum counts indicate the uppermost position of the rebounding test hammer 5. Therefore, in order to determine the rebounding height $h_{R1}$, it merely has to be determined after how many counts of this sequence the maximum counts are reached. This maximum then is related to a defined position within the optical pattern 8 on the test hammer 5, which position exactly defines the rebounding height $h_{R1}$.

As already mentioned, the strips 9, 16 of the optical pattern 8 are relatively coarse to avoid any affection of the optical scanning of the pattern by dirt on the hammer surface. The precision of the measurement, however, is much better than the width or extension of about 0.4 mm of the strips 9, 16 of the pattern. This is achieved by interpolation of the sequence of counts recorded during the second measuring cycle, as will be explained on the basis of FIG. 5.

In FIGS. 5A–5E five diagrams are exhibited, showing the counting sequences of five test strokes. In each of these diagrams a sequence of counts measured during the second measuring cycle is shown. On the horizontal axis of the diagrams the count indices (each index corresponding to a respective strip of the pattern) are indicated, whereas the vertical axis give the values of the counts. Therefore, as easily can be seen from these diagrams a total of 13 counts (with the indices 1 to 13) were recorded, among which the count (or strip) having the index No. 7 is nearest to the maximum.

Figure 5A:
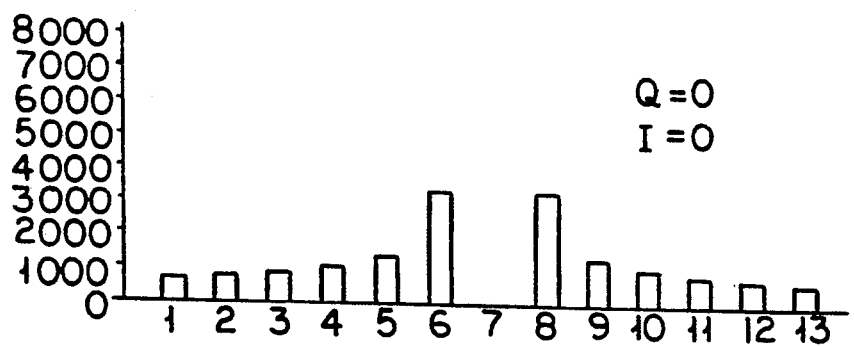
FIGS. 5A–5F are five diagrams and an interpolation curve for exhibiting the interpolation procedure.
Figure 5B:
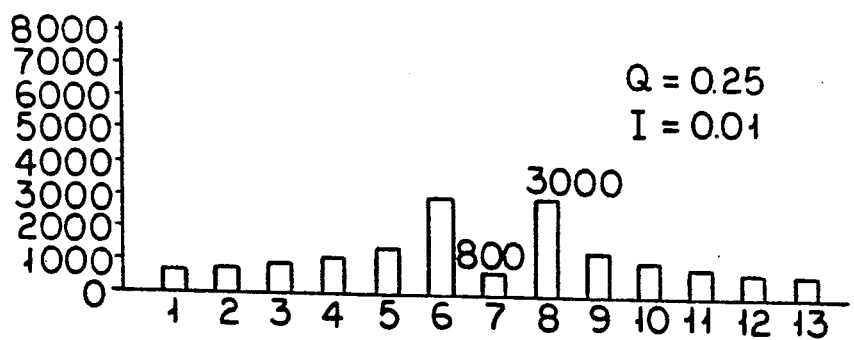
Figure 5C:
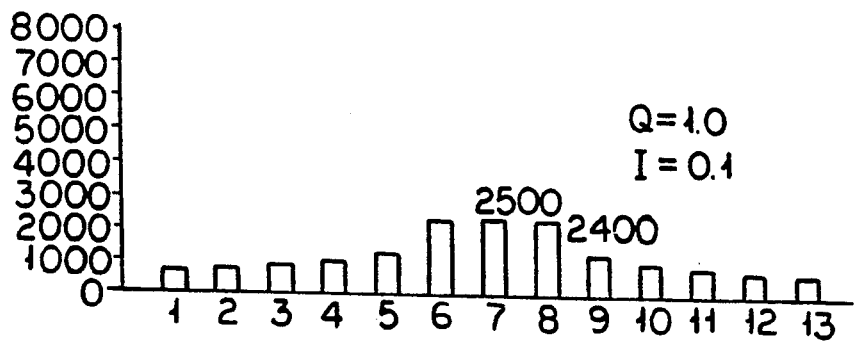
Figure 5D:
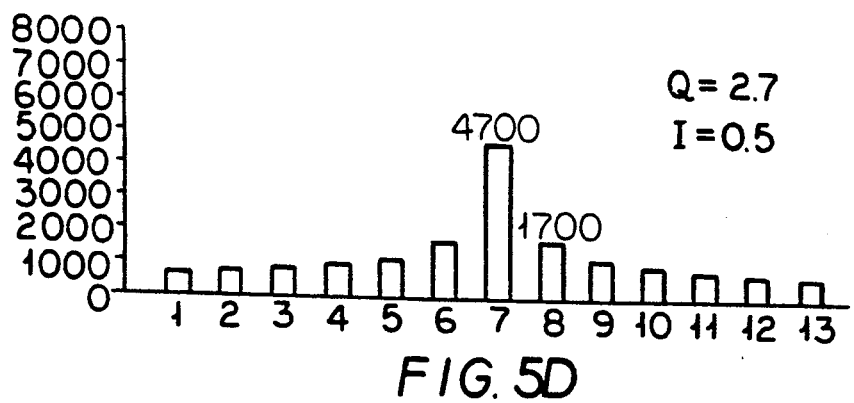
Figure 5E:
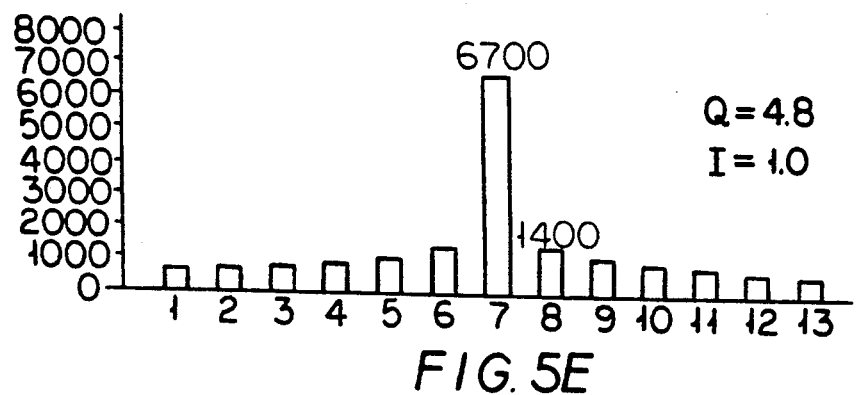

In the diagram of FIG. 5A a situation is shown, where at the maximum rebounding height of the hammer 5, the seventh strip of the pattern 8 just did not reach the optical sensor 18 so that there is no count with the index 7. In the following diagrams situations are shown in which the maximum rebounding height of the hammer 5 is slightly increased so that an increasing portion of the seventh strip of the pattern 8 reaches the optical sensor 21. Consequently, the respective count with the index 7 has an increasing value. In the last diagram the whole width of the seventh strip of the pattern 8, i.e. 0.4 mm, is detected by the optical sensor 18.

Figure 5F:
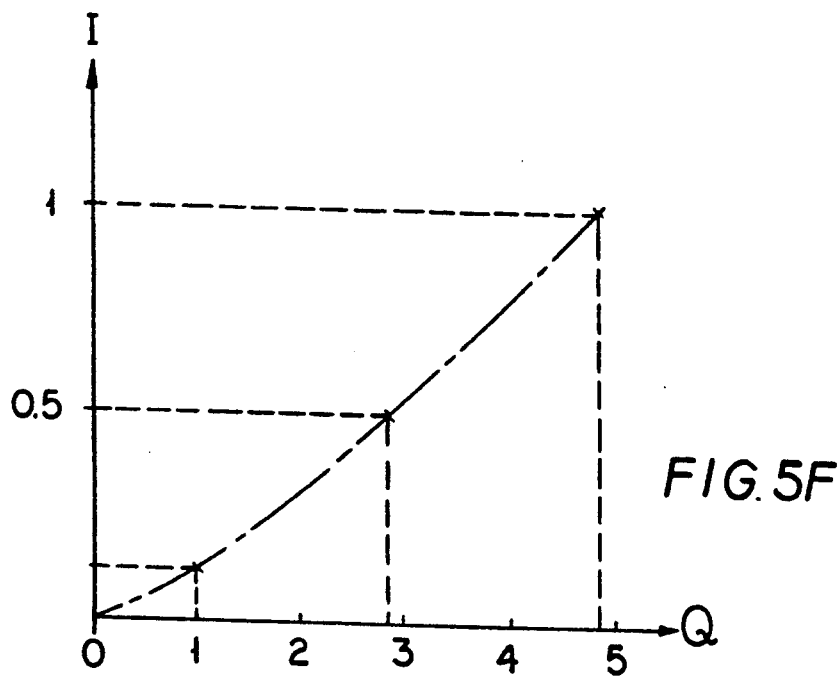

As is seen by this example it can easily determined by interpolation which portion of a certain strip of the pattern 8 (in the example of strip No. 7) has reached the optical sensor 18 when the test hammer 5 is at its maximum rebounding height. As an interpolation value e.g.

the quotient Q of the count value to be interpolated (strip No. 7) with the count value of the neighboring strip (strip No. 8) can be used. With an empirical interpolation curve as shown in FIG. 5F each interpolation value Q can be related to a defined portion I of the strip width of the highest strip detected by the light sensor 21. According to the diagram of FIG. 5A portion I is zero whereas in the last diagram it is one. Thereby, the maximum rebounding height $h_{R1}$ of the test hammer 5 is determined much more precisely than the structure of the optical pattern 8 itself would allow. The value of $h_R$ then is received by adding the measured adjustment value a to the measured and interpolated $h_{R1}$-value according to equation (2). The final R - value then is determined in accordance with equation (1).

An advantage of the described measuring principle wherein the individual counts are recorded for each light reflecting zone 16 and for each light absorbing recess 9 of the optical strip pattern 8 passing the optical sensor 18, is the possibility of a permanent control of the contrast of the pattern. This control is achieved by adding all counts of a sequence belonging to light reflecting zones 16 and all counts of the same sequence belonging to the light absorbing recesses 9 and by comparing these added values. If the quotient of these two added values is near 1, the optical contrast of the pattern is good. If this quotient is substantially less than 1 (i.e. the total counts belonging to the recesses 9 are substantially higher than the total counts belonging to the reflecting zones 16 of the optical pattern 8), this means that the contrast of the pattern has become bad (because the optical pattern e.g. is dirty).

This control function as well as the above described interpolation are performed by the timer/microprocessor 23 automatically based on the recorded sequences of counts and a respective routine, as explained above.

The described measuring apparatus even when used under rough conditions generates reproducible and precise R - values. It is especially uncritical against high mechanical shocks and vibrations caused by the impact of the test hammer 5. As already mentioned, the influence of wear and dirt on the optical pattern is permanently under control and false measurements are rejected.

While there are shown and described present preferred embodiments of the invention, it is to be distinctly understood that the invention is not limited thereto, but may be otherwise variously embodied and practiced within the scope of the following claims.

We claim:

1. An apparatus for measuring surface hardness of materials, comprising a housing with a moveable hammer of a given length arranged therein, a driving spring for driving said hammer, an impact pin with a front end and an opposite rear end, said hammer being driveable by means of said driving spring along a path in said housing for impact against said rear end of said impact pin, said front end of said impact pin being for placement on a surface to be measured, and a measuring device for measuring a rebound height of said hammer after impact, wherein said hammer is provided with an optical pattern over at least part of its length, said optical pattern comprising a plurality of regularly arranged alternating first and second zones, wherein said measuring device comprises an optical detector arranged adjacently of said path of the hammer for detecting the number said first and second zones which pass by said detector at least when the hammer is rebounded, and wherein said measuring device further comprises an evaluation circuit connected to said optical detector to determine, from said detected number, the maximum rebounding height of the hammer, said hammer having a cylindric outer surface defining a cylinder axis parallel to said path of the hammer, wherein said first and second zones are formed by a plurality of successive strips extending around the circumference of said cylindric outer surface an being alternatingly provided with light reflecting and light absorbing surface structures, said optical detector comprising a light emitter and a light sensor focused on said cylindric outer surface of said hammer, and wherein said first zones reflect light from said light emitter into said light sensor and said second zones prevent said reflection, respectively, dependent on the axial position of the hammer on its path and independent of the angular position of the hammer about said cylindric axis.

2. The apparatus of claim 1, wherein said second zones comprise groove shaped recesses provided with a light absorbing coating.

3. The apparatus of claim 1, wherein said optical detector comprises an infrared light emitter and an infrared light sensor and wherein said first zones of the pattern of the hammer are provided with an infrared light reflecting layer.

4. The apparatus of claim 1, wherein between each of successive ones of said first and second zones there is a transition in the light reflecting characteristics of said pattern, said optical detector detecting the passage thereby of said optical transitions, and said evaluation circuit comprises a timer which, at each said optical transition between a first and a second zone and vice versa detected by said optical detector, is stopped and started against immediately for measuring, in timer counts, the time between the passage past said detector of successive ones of said optical transitions, a store for storing the timer counts corresponding to each zone of the pattern, passing said detector and a processor for evaluation of said stored counts to determine the maximum rebounding height of the hammer.

5. The apparatus of claim 4, wherein said evaluation circuit comprises a processor for determining the maximum rebounding height of the hammer from said stored counts by means of an interpolation algorithm.

6. The apparatus of claim 4, wherein the optical detector is positioned at said housing relative to said path of said hammer such that in an impact position of said hammer said optical pattern is below said optical detector by a certain distance, which certain distance is determined by said timer and is used in said evaluation circuit for defining the position of said hammer at its impact with said pin.

7. The apparatus of claim 4, wherein said optical detector is positioned in said housing such that said optical pattern of said hammer is also evaluated while said hammer is being driven towards said impact for determining the velocity of said test hammer immediately before said impact, and wherein the determination of the maximum rebounding height of said hammer is accepted as valid only if said velocity is within a defined range.

8. The apparatus of claim 1, wherein said optical pattern has an upper end and a lower end and comprises at least at its lower end a zone having a length exceeding the length of said first and second zones for triggering said optical detector.

9. The apparatus of claim 8, wherein said optical pattern at is lower end comprises another zone of enlarged length.

10. The apparatus of claim 1, wherein said optical detector is positioned in said housing relative to said path of said hammer such that said optical pattern, in a first phase, is moved past said detector and evaluated over its complete length for correctness against predetermined criteria when said hammer is driven to impact against said impact pin, and, in a second phase, is moved past said detector and evaluated for a part of its length when said hammer rebounds, wherein said evaluation in said second phase is sued as a valid determination of the maximum rebounding height of the hammer only if in said first phase a correct evaluation of said optical pattern over its complete length was obtained.

* * * * *

UNITED STATES PATENT AND TRADEMARK OFFICE
CERTIFICATE OF CORRECTION

PATENT NO. : 5,176,026

DATED : JANUARY 5, 1993

INVENTOR(S) : Dietmar LEEB & Ueli BRUNNER

It is certified that error appears in the above-identified patent and that said Letters Patent is hereby corrected as shown below:

On the title page, after the Abstract "10 Claims" should be "14 Claims".

Column 10, add the following claims:

-- 11. An apparatus for measuring surface hardness of materials, comprising a housing with a moveable hammer of a given length arranged therein, a driving spring for driving said hammer, an impact pin with a front end and an opposite rear end, said hammer being driveable by means of said driving spring along in a path in said housing for impact against said rear end of said impact pin, said front end of said impact pin being for placement on a surface to be measured, and a measuring device for measuring a rebound

UNITED STATES PATENT AND TRADEMARK OFFICE
CERTIFICATE OF CORRECTION

PATENT NO. : 5,176,026
DATED : JANUARY 5, 1993
INVENTOR(S) : Dietmar LEEB & Ueli BRUNNER It is certified that error appears in the above-identified patent and that said Letters Patent is hereby corrected as shown below:

height of said hammer after impact, wherein said hammer is provided with an optical pattern over at least part of its length, said optical pattern comprising a plurality of regularly arranged alternating first and second zones, wherein said measuring device comprises an optical detector arranged adjacently of said path of the hammer for detecting the number of said first and second zones which pass by said detector at least when the hammer is rebounded, wherein said measuring device further comprises an evaluation circuit connected to said optical detector to determine, from said

UNITED STATES PATENT AND TRADEMARK OFFICE
CERTIFICATE OF CORRECTION

PATENT NO. : 5,176,026
DATED : JANUARY 5, 1993
INVENTOR(S) : Dietmar LEEB & Ueli BRUNNER It is certified that error appears in the above-identified patent and that said Letters Patent is hereby corrected as shown below:

detected number, the maximum rebounding height of the hammer, wherein said optical detector comprises a light emitter and a light sensor, wherein said first zones reflect light from said light emitter into said light sensor, said second zones prevent said reflection, and wherein said second zones comprises groove shaped recesses provided with a light absorbing coating.

12. An apparatus for measuring surface hardness of materials, comprising a housing with a moveable

UNITED STATES PATENT AND TRADEMARK OFFICE
CERTIFICATE OF CORRECTION

PATENT NO. : 5,176,026  
DATED : JANUARY 5, 1993  
INVENTOR(S) : Dietmar LEEB & Ueli BRUNNER It is certified that error appears in the above-identified patent and that said Letters Patent is hereby corrected as shown below:

hammer of a given length arranged therein, a driving spring for driving said hammer, an impact pin with a front end and an opposite rear and, said hammer being driveable by means of said driving spring along a path in said housing for impact against said rear end of said impact pin, said front end of said impact pin being for placement on a surface to be measured, and a measuring device for measuring a rebound height of said hammer after impact, wherein said hammer is provided with an optical pattern over at least part of its length, said optical pattern comprising a plurality of

UNITED STATES PATENT AND TRADEMARK OFFICE
CERTIFICATE OF CORRECTION

PATENT NO. : 5,176,026
DATED : JANUARY 5, 1993
INVENTOR(S) : Dietmar LEEB & Ueli BRUNNER It is certified that error appears in the above-identified patent and that said Letters Patent is hereby corrected as shown below:

regularly arranged alternating first and second zones, wherein said measuring device comprises an optical detector arranged adjacently of said path of the hammer for detecting the number of said first and second zones which pass by said detector at least when the hammer is rebounded, wherein said measuring device further comprises an evaluation circuit connected to said optical detector to determine, from said detected number, the maximum rebounding height of the hammer, wherein between each of successive ones of said first and second zones there is a transition in the light reflect-

UNITED STATES PATENT AND TRADEMARK OFFICE
CERTIFICATE OF CORRECTION

PATENT NO. : 5,176,026
DATED : JANUARY 5, 1993
INVENTOR(S) : Dietmar LEEB & Ueli BRUNNER It is certified that error appears in the above-identified patent and that said Letters Patent is hereby corrected as shown below:

ing characteristics of said pattern, said optical detector detecting the passage thereby of said optical transitions, and said evaluation circuit comprises a timer which, at each said optical transition between a first and a second zone and vice versa detected by said optical detector, is stopped and started again immediately for measuring, in timer counts, the time between the passage past said detector of successive ones of said optical transitions, a store for storing the timer counts corresponding to each zone of the pattern passing said detector, and a processor for evalua-

UNITED STATES PATENT AND TRADEMARK OFFICE
CERTIFICATE OF CORRECTION

PATENT NO. : 5,176,026
DATED : JANUARY 5, 1993
INVENTOR(S) : Dietmar LEEB & Ueli BRUNNER It is certified that error appears in the above-identified patent and that said Letters Patent is hereby corrected as shown below:

tion of said stored counts to determine the maximum rebounding height of the hammer.

13. An apparatus for measuring surface hardness of materials, comprising a housing with a moveable hammer of a given length arranged therein, a driving spring for driving said hammer, an impact pin with a front end and an opposite rear end, said hammer being driveable by means of said driving spring along a path in said housing for impact against said rear end of said impact pin, said front

UNITED STATES PATENT AND TRADEMARK OFFICE
CERTIFICATE OF CORRECTION

PATENT NO. : 5,176,026
DATED : JANUARY 5, 1993
INVENTOR(S) : Dietmar LEEB & Ueli BRUNNER It is certified that error appears in the above-identified patent and that said Letters Patent is hereby corrected as shown below:

end of said impact pin being for placement on a surface to be measured, and a measuring device for measuring a rebound height of said hammer after impact, wherein said hammer is provided with an optical pattern over at least part of its length, said optical pattern comprising a plurality of regularly arranged alternating first and second zones, wherein said measuring device comprises an optical detector arranged adjacently of said path of the hammer for detecting the number of said first and second zones which pass by said detector at least when the hammer is rebounded, and wherein

UNITED STATES PATENT AND TRADEMARK OFFICE
CERTIFICATE OF CORRECTION

PATENT NO. : 5,176,026
DATED : JANUARY 5, 1993
INVENTOR(S) : Dietmar LEEB & Ueli BRUNNER It is certified that error appears in the above-identified patent and that said Letters Patent is hereby corrected as shown below:

said measuring device further comprises an evaluation circuit connected to said optical detector to determine, from said detected number, the maximum rebounding height of the hammer, wherein said optical pattern has an upper end and a lower end and comprises at least at its lower end a zone having a length exceeding the length of said first and second zones for triggering said optical detector.

14. An apparatus according to claim 15, wherein said optical detector is positioned in said housing

UNITED STATES PATENT AND TRADEMARK OFFICE
CERTIFICATE OF CORRECTION

PATENT NO. : 5,176,026
DATED : JANUARY 5, 1993
INVENTOR(S) : Dietmar LEEB & Ueli BRUNNER It is certified that error appears in the above-identified patent and that said Letters Patent is hereby corrected as shown below:

such that said optical pattern of said hammer is also evaluated while said hammer is being driven towards said impact for determining the velocity of said test hammer immediately before said impact, and wherein the determination of the maximum rebounding height of said hammer is accepted as valid only if said velocity is within a defined range.--

Signed and Sealed this

Twenty-first Day of December, 1993

*Attest:*

BRUCE LEHMAN

*Attesting Officer*     *Commissioner of Patents and Trademarks*